(12) United States Patent
Okada et al.

(10) Patent No.: US 6,838,580 B2
(45) Date of Patent: Jan. 4, 2005

(54) OPIOID DERIVATIVE

(75) Inventors: Yoshio Okada, Akashi (JP); Yuko Tsuda, Akashi (JP); Toshio Yokoi, Akashi (JP); Sharon D. Bryant, Chapel Hill, NC (US); Lawrence H. Lazarus, Durham, NC (US)

(73) Assignee: Teikoku Seiyaku Co., Ltd., Kagawa-ken (JP)

( * ) Notice: Subject to any disclaimer, the term of this patent is extended or adjusted under 35 U.S.C. 154(b) by 359 days.

(21) Appl. No.: 10/058,192

(22) Filed: Jan. 29, 2002

(65) Prior Publication Data

US 2003/0171302 A1 Sep. 11, 2003

(51) Int. Cl.$^7$ .................. C07C 233/05; A61K 31/16
(52) U.S. Cl. ................. 564/157; 514/616; 514/19
(58) Field of Search ................. 564/157; 514/616, 514/19

(56) References Cited

U.S. PATENT DOCUMENTS 5,272,175 A * 12/1993 Hansen et al. ............... 514/487

FOREIGN PATENT DOCUMENTS

JP          2001-122895          5/2001

OTHER PUBLICATIONS

Yoshio Okada et al.; Tetrahedron, vol. 55, 1999, pp. 14391–14406.

* cited by examiner

*Primary Examiner*—Shailendra Kumar
(74) *Attorney, Agent, or Firm*—Birch, Stewart, Kolasch & Birch, LLP

(57) ABSTRACT

1. A peptide derivative represented by the following formula (1) or a salt thereof;

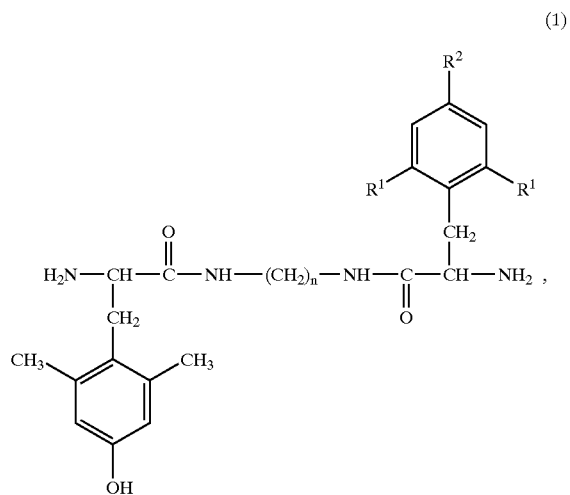

wherein $R^1$ is hydrogen atom or methyl group, $R^2$ is hydrogen atom or hydroxy group and n is an integer of 1-8, provided that $R^1$ is hydrogen atom when $R^2$ is hydrogen atom, which has specific and high binding affinity with the $\mu$-opioid receptor.

6 Claims, No Drawings

OPIOID DERIVATIVE

TECHNICAL FIELD

The present invention relates to a new peptide derivative or its salt which has excellent physiological activity via the opioid receptor, especially shows binding affinity to the opioid receptor in lower concentration. Further the present invention relates to a medical composition containing said peptide as an active ingredient and its medical use.

PRIOR ART

It is known that peptides show various physiological activities by changing their amino acid sequence. A peptide mimetic prepared by changing a peptide-component, an amino acid with another amino acid or other substituent, tends to show another specific activity. Many studies on these peptides, generally called opioid peptides such as enkephalin, etc., which are present in brain and participate in analgesic activity etc., have been carried out, as well as with opioid mimetics, which are synthetic opioid peptides resembling naturally occurring compounds.

It is reported that expression of analgesic activity occurs by interaction between ligand and receptor.

Morphine has been known as an opioid-receptor activating substance, and opioid type analgesics, morphine homologues have been clinically used for inhibition of cancer pain, acute pain after skin-grafting or post varicella-zoster.

However, these analgesics show severe side effects such as central nervous system depressive activity, leiomyotention of digestive tract, addiction, toleration etc. and therefore, further improved analgesics, in many fields especially such as anaphase of cancer, pain after post varicella-zoster are strongly desired.

DETAILED DESCRIPTION OF INVENTION

The present inventors have recently invented to form a pyrazinone ring from dipeptidyl chloromethyl ketone and have succeeded in preparing opioid mimetics therefrom (Okada et al., Tetrahedron Lett. 55, 14391–14406 (1999)). Some compounds among them were found to be weak in activity but to bind specifically with the $\mu$-opioid receptor.

Furthermore, the present inventors have studied with expectation for preparing more selective opioid mimetic analgesics with higher activity using the simple alkyl chain instead of said pyrazinone ring. Namely, the present inventors planed to introduce tyrosine, phenylalanine or 2,6-dimethyltyrosine (Salvadori et al., Molecular Medicine, 1, 678–689(1995)) at the both amino groups of alkanediamine ($NH_2$-alkyl-$NH_2$) for the purpose to enhance specific and high binding affinity toward the $\mu$-opioid receptor.

As a result, it has been found that peptide derivatives represented by the following formula (1) have specific and high binding affinity with the $\mu$-opioid receptor and show different analgesic activity from morphine, and the present invention has been completed.

The present invention relates to a peptide derivative represented by the following formula (1) or a salt thereof;

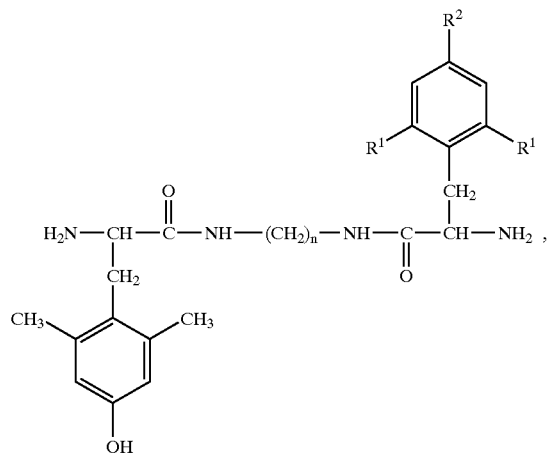

(1)

wherein $R^1$ is hydrogen atom or methyl group, $R^2$ is hydrogen atom or hydroxy group and n is an integer of 1-8, provided that $R^1$ is hydrogen atom when $R^2$ is hydrogen atom, which shows specific and high binding affinity with the $\mu$-opioid receptor.

Further, the present invention relates to a pharmaceutical composition containing at least one peptide derivative represented by the formula (1) or one salt thereof as an active ingredient.

Further, the present invention relates to a $\mu$-opioid receptor agonist activator containing at least one peptide derivative represented by the formula (1) or one salt thereof as an active ingredient.

Further, the present invention relates to a method for inhibiting or moderating pain by administering at least one peptide derivative represented by the formula (1) or one salt thereof having $\mu$-opioid receptor agonist activation activity as an active ingredient in an effective dosage to a patient having pain or suffering from nervous defect disease (neuropathy) related to $\mu$-opioid receptor activation.

EMBODIMENT OF INVENTION

The peptide derivative in the present invention consists of binding 2,6-dimethyltyrosine (abbreviated as Dmt) at one amino group of diaminoalkane, and binding tyrosine, phenylalanine, or 2,6-dimethyltyrosine at the other amino group of the diaminoalkane, and all the amino acids are levorotary.

The peptide derivative represented by the formula (1) is easily prepared by the liquid phase method.

For example, a peptide is prepared by coupling 1,4-dimethylalkane with Boc-Dmt-OH by BOP (benzotriazol-1-yl-oxy-tris(dimethylamino) phosphoniumhexafluorophosphate), and thus prepared peptide is subject to TFA-treatment and hydrochloric acid-treatment in dioxane to give a peptide derivative (1) wherein $R^1$ is methyl group and $R^2$ is hydroxy group.

The synthesis scheme of the above compound, e.g. the hydrochloride is shown below.
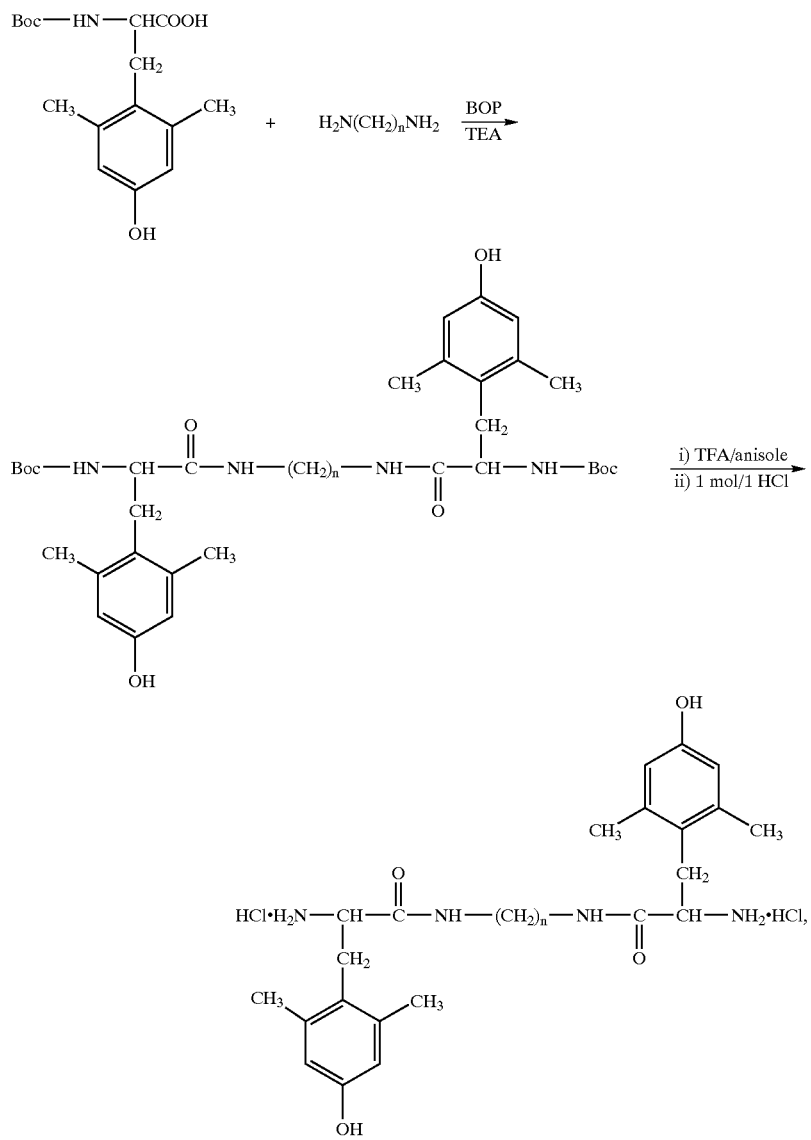
wherein n is an integer of 1-8.
The synthesis scheme of the opioid derivatives (1) of the present invention, wherein $R^1$ is hydrogen atom and $R^2$ is hydrogen atom or hydroxy group and n is an integer of 4 is shown below.
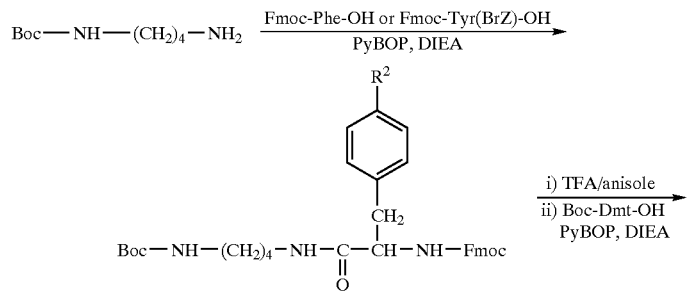

-continued

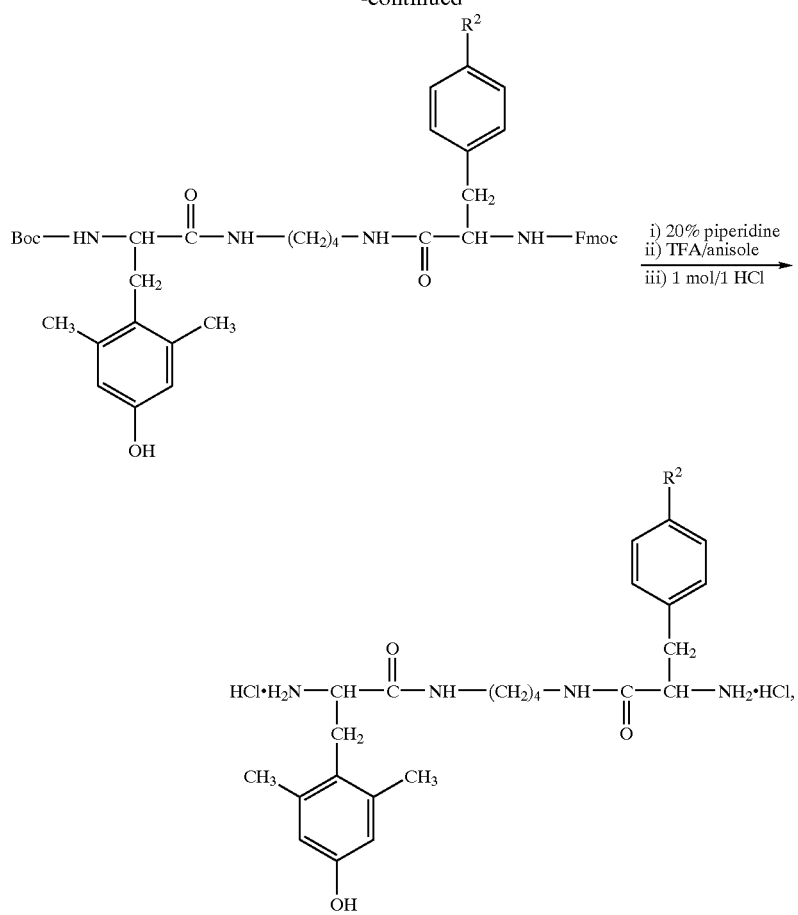

wherein R² is hydrogen atom or hydroxy group.

In the method for preparation of the peptide derivative (1) of the present invention, the objective peptide derivative and an intermediate thereof are isolated and purified by being appropriately combined with various methods such as ion chromatography, gel chromatography, reverse phase chromatography, recrystallization, extraction, etc.

Thus obtained peptide derivative (1) of the present invention can be converted into a salt thereof using an organic or inorganic acid according to the conventional method.

The preferable compound of the present invention is a peptide derivative (1) of the present invention wherein n is an integer of 4 to 6, and further preferably R² is hydroxy group and furthermore preferably R¹ is methyl group.

The preferable salt is a pharmaceutically acceptable salt, such as hydrochloride or methanesulfonate.

The starting material, dimethyltyrosine can be prepared in accordance with a method described in Dygos et al. (Synthesis, 741 (1991)).

The peptide derivative (1) of the present invention or a salt thereof is not described in any publication, and has specific and high binding affinity with the μ-opioid receptor and exhibits morphine like-physiological activity, such as analgesic activity.

Therefore, the peptide derivative (1) of the present invention or a salt thereof exhibits analgesic activity and the central nervous system or peripheral nervous system response which the opioid peptide expresses via its receptor, such as physiological activities, e.g., anesthesia, pulse, digestion mechanism, hormone releasing control, cardiac muscle contraction control.

The peptide derivative (1) of the present invention or a salt thereof can be used as analgesics and as a therapeutic or prophylactic drug for diseases with the nervous system defect related to other opioid receptor activation.

The peptide derivative (1) of the present invention or a salt thereof is orally, paraorally, intrarectally, sublingually or topically administered, or is administered by epidural injection in the spinal cord or by intra-arachinoid injection. The peptide derivative (1) of the present invention or a salt thereof can be combined with other ingredients suitable for the purposed preparation (form) to be administered to the patient.

Dosage of the peptide derivative (1) of the present invention or a salt thereof depends on age, degree of diseases etc., but is usually 0.01–500 mg/kg/day and may thus be divided.

The following abbreviations used in the present specification mean as follows;

AcOEt: Ethyl acetate
Boc: tert-Butoxycarbonyl
BOP: Benzotriazol-1-yl-oxy-tris(dimethylamino) phosphonium hexafluorophosphate
BrZ: 2-Bromobenzyloxycarbonyl
DIEA: Diisopropylethylamine
DMF: Dimethylformamide
Dmt: 2,6-dimethyl-L-tyrosine
Fmoc: 9-Fluorenylmethoxycarbonyl
MeCN: Acetonitrile
PyBOP: Benzotriazol-1-yl-oxy-tris(pyrrolidino) phosphonium hexafluorophosphate Et₃N: Triethylamine
TFA: Trifluoroacetic acid
HEPES: N-2-Hydroxyethylpiperazine-N'-2-ethane sulfonic acid
GDP: Guanosine 5'-diphosphate
DAGO: H-Tyr-D-Ala-Gly-MePhe-Gly-ol
DPDPE: H-Tyr-cyclo(D-Pen-Gly-Phe-D-Pen)

The present invention is illustrated by the following examples, reference examples and experimental tests, but is not limited by them.

EXAMPLE

General Procedure

Melting points were determined on a Yanagimoto micro-melting point apparatus without correction.

Optical rotations were measured with an automatic polarimeter, model DIP-360 (Japan Spectroscopic Co.).

Matrix assisted laser desorption time-of-flight mass spectra (MALDI-TOF-MS) were obtained on a Kratos MALDI II mass spectrometer (Kratos Analytical).

NMR: $^1$H-(500 MHz) and $^{13}$C-(125 MHz)NMR spectra were recorded on a Bruker ARX500 spectrometer.

Chemical shifts are expressed as ppm down field from tetramethylsilane, used as an internal standard (δ-value). The J values are given in Hz. The $^{13}$C signals were assigned with the aid of distortionless enhancement by polarization transfer (DEPT), and 2D experiments, and multiplicities are indicated by a p (primary), s (secondary), t (tertiary) or q (quaternary). Waters model 600E was used for analytical or preparative HPLC. Peptides were analyzed by reverse phase HPLC on a COSMOSIL C18 column (4,6×250 mm, Nakarai) or YMC R&D R-ODS-5-A (4.6×250 mm).

Retention time was shown as tR (C) or tR (Y), respectively. The column was eluted by using a linear gradient from 10% acetonitrile in water, containing 0.05% TFA by increasing 1% acetonitrile concentration in one min. at a flow rate of 1 ml/min; Detection was at 220 nm. On TLC (Kieselgel 60G. Merck), $Rf^1$, $Rf^2$, $Rf^3$, $Rf^4$ and $Rf^5$ values refer to the systems of $CHCl_3$, MeOH and AcOH (90:8:2); $CHCl_3$, MeOH and $H_2O$ (89:10:1); $CHCl_3$, MeOH and $H_2O$ (8:3:1, lower phase); n-BuOH, AcOH and $H_2O$ (4:1:5, upper phase); n-BuOH, AcOH, pyridine and $H_2O$ (4:1:1:2), respectively.

0.1% Ninhydrin-Aceton Solution was used for detection of amino group. Hydrogen bromide-Ninhydrin Method was used for detection of Boc-protecting group.

Example 1

1) 1,4-Bis-(N$^α$-Boc-Dmt-amino)butane

BOP reagent (700 mg, 1.6 mmol) was added to a solution of N$^α$-Boc-Dmt-OH (500 mg, 1.6 mmol), 1,4-diaminobutane (60 mg, 0.68 mmol) in DMF (15 ml) containing Et₃N (0.66 ml, 4.7 mmol) at room temperature. The reaction was stirred for 18 hr at room temperature. After removal of the solvent, the residue was extracted with AcOEt, which was washed with 10% citric acid, 5% $Na_2CO_3$ and water, dried over $Na_2SO_4$ and evaporated down. Petroleum ether was added to the residue to obtain a precipitate, which was collected by filtration. The crude product in $CHCl_3$ (5 ml) was applied to a silica gel column (BW-127ZH, 3×16 cm), which was equilibrated and eluted with $CHCl_3$ (2100 ml). After removal of the solvent of the effluent (1,500 ml–2,100 ml), petroleum ether was added to the residue to yield crystals, which were collected by filtration, yield 300 mg (58.4%), mp 214–217° C., $Rf^1$ 0.46, $Rf^2$ 0.32.

Anal. Calcd for $C_{36}H_{54}N_4O_8.0.5H_2O$: C, 63.6; H, 8.15; N, 8.24. Found: 63.8; H, 8.16; N, 8.04.

2) 1,4-Bis-(Dmt-amino)butane.2HCl

A solution of 1,4-bis-(N$^α$-Boc-Dmt-amino)butane (200 mg, 0.30 mmol) in TFA (1.0 ml, 13 mmol) containing anisole (0.10 ml, 0.90 mmol) was stirred for 1 hr at room temperature. Ether was added to a solution to form a precipitate, which was collected by filtration and dried in vacuo. The solution of the product in 1 mol/l HCl (0.6 ml) was lyophilized to yield a fluffy powder, yield 110 mg (68%), $Rf^4$ 0.19, $Rf^5$ 0.32, tR (C) 14.97 min. TOF-MS m/z: 472.0 (M+1)$^+$ (Calcd for $C_{26}H_{38}N_4O_4$: 470.6).

Example 2

1) 1-Boc-amino-4-(N$^α$-Fmoc-Phe-amino)butane 1-(Boc-amino)-4-aminobutane (2.0 g, 10 mmol), N$^α$-Fmoc-Phe-OH (4.6 g, 12 mmol), PyBOP (6.24 g, 10 mmol) and HOBt (1.6 g, 12 mmol) were dissolved in DMF (50 ml) containing DIEA (4.2 ml, 24 mmol). The reaction mixture was stirred for 15 hr at room temperature. After removal of the solvent, AcOEt was added to the residue to obtain a precipitate, which was collected by filtration and recrystallized from EtOH, yield 3.0 g (45%), mp 165–167° C., $Rf^1$ 0.66.

Anal. Calcd for $C_{33}H_{39}N_3O_5.0.25H_2O$: C, 70.5; H, 7.08; N, 7.47. Found: C, 70.5; H, 7.06; N, 7.64.

2) 1-N$^α$-(Boc-Dmt-amino-4-(N$^α$-Fmoc-Phe-amino)butane

N$^α$-Boc-Dmt-OH (460 mg, 1.50 mmol), 1-amino-4-(N$^α$-Fmoc-Phe-amino)butane.TFA [prepared from 1-Boc-amino-4-(N$^α$-Fmoc-Phe-amino)butane (830 mg, 1.50 mmol), anisole (0.25 ml, 2.3 mmol) and TFA (2.2 ml, 30 mmol) as usual], PyBOP (930 mg, 1.8 mmol) and HOBt (270 mg, 1.8 mmol) were dissolved in DMF (10 ml) containing DIEA (0.50 ml, 3.80 mmol). The reaction mixture was stirred for 15 hr at room temperature. After removal of the solvent, the residue was extracted with AcOEt, which was washed with 10% citric acid, 5% $Na_2CO_3$ and water, dried over $Na_2SO_4$ and evaporated down. Petroleum ether was added to the residue to yield a precipitate. The crude product in $CHCl_3$ (5 ml) was applied to a silica gel column (YMC 70–230 mesh, 3×16 cm), which was equilibrated and eluted with $CHCl_3$. After removal of the solvent of the effluent (210 ml), petroleum ether was added to the residue to give crystals, which were collected by filtration, yield 600 mg (63%), mp 201–203.5° C., $Rf^1$ 0.52.

Anal. Calcd for $C_{44}H_{52}N_4O_7.0.3H_2O$: C, 70.0; H, 7.03; N, 7.42. Found: C, 70.0; H, 7.44; N, 7.48.

3) 1-Dmt-amino-4-Phe-aminobutane.2HCl 1-(N$^α$-Boc-Dmt-amino)-4-(N$^α$-Fmoc-Phe-amino)butane (500 mg, 0.78 mmol) was treated with 20% piperidine in DMF (11.5 ml) for 2 hr at room temperature. After removal of the solvent, ether was added to the residue to obtain a precipitate, which was collected by filtration ($Rf^1$ 0.16, $Rf^3$ 0.70). This product (300 mg, 0.57 mmol) was dissolved in TFA (1.0 ml, 13 mmol) containing anisole (0.10 ml, 0.90 mmol) and the solution was stirred for 1 hr at room temperature. Ether was added to the solution to give a precipitate, which was collected by filtration. The crude product was purified with HPLC and lyophilized from 1 mol/l HCl to obtain fluffy amorphous powder, yield 220 mg (56%), $Rf^4$ 0.30, $Rf^5$ 0.46, tR(C) 17.07 min. TOF-MS m/z: 427.5 (M+1)$^+$ (Calcd for $C_{24}H_{34}N_4O_3$: 426.6).

$^1$H-NMR (free compound, DMSO-d6)δ: 8.648 (1H, t, J=5.5 HZ, NH of Phe amide), 7.997 (1H, t, J=5.5, NH of Dmt amide), 7.32–7.23 (5H, m, aromatic H of Phe), 6.441 (2H, s, aromatic H of Dmt), 4.043 (1H, t, J=7.0, α-H of Phe), 3.711 (1H, dd, J=9.3, 6.4, α-H of Dmt), 3.071 (2H, d, J=7.0, β-$CH_2$ of Phe), 3.01–2.70 (6H, m, 1,4-$CH_2$+β-$CH_2$ of Dmt), 2.187 (6H, s, diMe of Dmt), 1.16–1.01 (4H, m, 2,3-$CH_2$), 13C-NMR (DMSO-d6) δ: 167.91 (q, >C=O of Dmt), 167.52 (q, >C=O of Tyr), 155.54 (q, >C=, 4 of Dmt), 138.14 (q, >C=, 2,6 of Dmt), 135.10 (t, >C=, 1 of Phe), 129.42 (t, H—C=, 2,6 of Phe), 128.25 (t, H—C=, 3,5 of Phe), 126.84 (t, H—C=, 4 of Phe), 122.08 (q, >C=, 1 of Dmt), 114.80 (t, H—C=, 3,5 of Dmt), 53.39 (t, H—C<, α of Phe), 51.65 (t, H—C<, α of Dmt), 38.09 (s, —CH$_2$—, 1 or 4 CH$_2$), 38.05 (s, —CH$_2$—, 4 or 1 CH$_2$), 36.83 (s, β of Phe), 30.44 (s, β of Dmt), 25.52 (s, —CH$_2$—, 2 or 3 CH$_2$), 25.48 (s, —CH$_2$—, 3 or 2 CH$_2$), 19.90 (p, —CH$_3$, diMe of Dmt).

Example 3

1) 1-Boc-amino-4-N$^\alpha$-Fmoc-Tyr(BrZ)-aminobutane

1-Boc-amino-4-aminobutane (0.94 g, 5 mmol), N$^\alpha$-Fmoc-Tyr(BrZ)-OH (3.1 g, 12 mmol), and PyBOP (6.24 g, 12 mmol) were dissolved in DMF (30 ml) containing DIEA (1.7 ml, 10 mmol). The reaction mixture was stirred for 15 hr at room temperature. After removal of the solvent, AcOEt and 5% Na$_2$CO$_3$ were added to the residue to give crystals, which were collected by filtration and recrystallized from EtOH, yield 3.1 g (80%), mp 145–148° C., Rf$^1$ 0.80, Rf$^2$ 0.80.

Anal. Calcd for C$_{41}$H$_{44}$N$_3$O$_8$Br: C, 62.6; H, 5.63; N, 5.34. Found: C, 62.6; H, 5.65; N, 5.25.

2) 1-(N$^\alpha$-Boc-Dmt-amino)-4-N$^\alpha$-Fmoc-Tyr(BrZ)-aminobutane

N$^\alpha$-Boc-Dmt-OH (550 mg, 1.80 mmol), 1-amono-4-[N$^\alpha$-Fmoc-Tyr(BrZ)]-aminobutane.TFA [prepared from Boc-amino-4-[N$^\alpha$-Fmoc-Tyr(BrZ)]-aminobutane (1.2 g, 1.5 mmol), anisole (0.25 ml, 2.3 mmol) and TFA (2.2 ml, 30 mmol) as usual], and PyBoP (1.12 g, 2.2 mmol) were dissolved in DMF (20 ml) containing DIEA (0.88 ml, 5.1 mmol). The reaction mixture was stirred for 15 hr at room temperature. After removal of the solvent, the residue was extracted with AcOEt, which was washed with 10% citric acid, 5% Na$_2$CO$_3$ and water, dried over Na$_2$SO$_4$ and evaporated down. Ether was added to the residue to yield crystals, which were collected by filtration and recrystallized from EtOH, yield 1.1 g (63%), mp 186–190° C., Rf$^1$ 0.77.

Anal Calcd for C$_{52}$H$_{57}$N$_4$O$_{10}$Br: C, 63.9; H, 5.87; N, 5.72. Found: C, 63.6; N, 5.84; N, 5.50.

3) 1-(Dmt-amino)-4-Tyr-aminobutane.2HCl

1-N$^\alpha$-Boc-Dmt-amino-4-N$^\alpha$-Fmoc-Tyr(BrZ)-aminobutane (600 mg, 0.61 mmol) was treated with 20% piperidine in DMF (15 ml) for 2 hr at room temperature. After removal of the solvent, ether was added to the residue to obtain a precipitate, which was collected by filtration (Rf$^1$ 0.04, Rf$^3$ 0.57). A solution of the resulting product (220 mg, 0.41 mmol) in TFA (1.0 ml, 13 mmol) was stirred for 1 hr at room temperature. Ether was added to the solution to give a precipitate, which was collected by filtration, dried in vacuo and purified with HPLC. The purified product was lyophilized from 1 mol/l HCl to yield a white fluffy amorphous powder, yield 100 mg (32%), Rf$^4$ 0.20, RF$^5$ 0.36, tR (C) 15.78 min. TOF-MS m/z: 443.8 (M+1)$^+$ (Calcd for C$_{24}$H$_{34}$N$_4$O$_4$: 442.5).

$^1$H-NMR (free compound, DMSO-d6) δ: 8.541 (1H, t, J=5.4 HZ, NH of Tyr amide), 7.972 (1H, t, J=5.4, NH of Dmt amide), 7.046 (2H, d-like, J=8.5, 2,6 H of Tyr), 6.717 (2H, d-like, J=8.5, 3,5 H of Tyr), 6.434 (2H, s,3,5 H of Dmt), 3.923 (1H, t, J=7.0, α-H of Tyr), 3.701 (1H, dd, J=10.6, α-H of Dmt), 3.02–2.79 (8H, m, 1,4-CH$_2$+β-CH$_2$ of Tyr and Dmt), 2.184 (6H, s, diMe of Dmt), 1.18–1.03 (4H, m, 2,3-CH$_2$), $^{13}$C-NMR (DMSO-d6) δ: 167.91 (q, >C=O of Dmt), 167.63 (q, >C=O of Tyr), 156.40 (q, >C=, 4 of Tyr), 155.52 (q, >C=, 4 of Dmt), 138.16 (q, >C=, 2,6 of Dmt), 130.31 (t, H—C=, 2,6 of Tyr), 124.89 (q, >C=, 1 of Tyr), 122.08 (q, 1 of Dmt), 115.15 (t, H—C=, 3,5 of Tyr), 114.81 (t, H—C=, 3,5 of Dmt), 53.69 (t, H—C<, α of Tyr), 51.67 (t, H—C<, α of Dmt), 38.11 (s, —CH$_2$—, 1 or 4 CH$_2$), 38.05 (s, —CH$_2$—, 4 or 1 CH$_2$), 36.12 (s, β of Tyr), 30.45 (s, β of Dmt), 25.56 (s, —CH$_2$—, 2 or 3 CH$_2$), 25.52 (s, —CH$_2$—, 3 or 2 CH$_2$), 19.88 (p, —CH$_3$, diMe of Dmt).

Example 4

1) 1,6-Bis(N$^\alpha$-Boc-Dmt-amino)hexane

N$^\alpha$-Boc-Dmt-OH (500 mg, 1.6 mmol), 1,6-diaminohexane (92 mg, 0.80 mmol) and PyBOP (1.0 g, 1.9 mmol) were dissolved in DMF (15 ml) containing Et$_3$N (0.27 ml, 1.9 mmol). The reaction mixture was stirred for 18 hr at room temperature. After removal of the solvent, the residue was extracted with AcOEt, which was washed with 10% citric acid, 5% Na$_2$CO$_3$ and water, dried over Na$_2$SO$_4$ and evaporated down. Petroleum ether was added to the residue to give a precipitate, which was collected by filtration. The crude product in AcOEt-n-hexane (1:1, 5 ml) was applied to a silica gel column(BW-127ZH, 3×16 cm), equilibrated and eluted with AcOEt-n-hexane (1:1, 300 ml). After removal of the solvent of the effluent (1–200 ml), petroleum ether was added to the residue to form a precipitate, which was collected by filtration, yield 300 mg (53%), mp 183–186° C., Rf$^1$ 0.52, Rf$^2$ 0.08.

Anal. Calcd for C$_{38}$H$_{58}$N$_4$O$_8$.0.25H$_2$O: C, 64.9; H, 8.37; N, 7.96. Found: C, 65.0; H, 8.22; N, 7.78.

2) 1,6-Bis(Dmt-amino)hexane.2HCl

A solution of 1,6-bis(N$^\alpha$-Boc-Dmt-amino)hexane (150 mg, 0.21 mmol) and anisole (0.10 ml, 0.90 mmol) in TFA (1.0 ml, 13 mmol) was stirred for 1 hr at room temperature. Ether was added to the solution to form a precipitate, which was collected by filtration, dried in vacuo and lyophilized from 1 mol/l HCl, yield 90 mg (75%), Rf$^4$ 0.21, Rf$^5$ 0.42, tR (C) 18.15 min. TOF-MS m/z: 499.2 (M+1)$^+$ (Calcd for C$_{28}$H$_{42}$N$_4$O$_4$: 498.6).

Example 5

1) 1,2-Bis(N$^\alpha$-Boc-Dmt-amino)ethane

N$^\alpha$-Boc-Dmt-OH (500 mg, 1.6 mmol), 1,2-diaminoethane (50 µl, 0.80 mmol), BOP (840 mg, 1.9 mmol) and HOBt (260 mg, 1.9 mmol) were dissolved in DMF (15 ml) containing Et$_3$N (0.54 ml, 3.8 mmol). The reaction mixture was stirred for 18 hr at room temperature. After removal of the solvent, the residue was extracted with AcOEt, which was washed with 10% citric acid, 5% Na$_2$CO$_3$, and water, dried over Na$_2$SO$_4$ and evaporated down. Petroleum ether was added to the residue to yield crystals, which were collected by filtration and recrystallized from EtOH, yield 300 mg (58%), mp 201–205° C., Rf$^1$ 0.48.

Anal. Calcd for C$_{34}$H$_{50}$N$_4$O$_8$.0.5H$_2$O: C, 62.7; H, 7.88; N, 8.59. Found: C, 62.5; H, 7.80; N, 8.30.

2) 1,2-Bis(Dmt-amino)ethane.2TFA

A solution of 1,2-bis(N$^\alpha$-Boc-Dmt-amino)ethane (200 mg, 0.30 mmol) and anisole (0.1 ml, 0.90 mmol) in TFA (1.0 ml, 13 mmol) was stirred for 1 hr at room temperature. Ether was added to the solution to form a precipitate, which was collected by filtration, dried in vacuo and lyophilized from water, yield 120 mg (60%), Rf$^4$ 0.14, Rf$^5$ 0.58, tR (C) 13.8 min. TOF-MS m/z: 443.6 (M+1)$^+$ (Calcd for C$_{24}$H$_{34}$N$_4$O$_4$: 442.5).

Example 6

1) 1,8-Bis(N$^\alpha$-Boc-Dmt-amino)octane

N$^\alpha$-Boc-Dmt-OH (500 mg, 1.6 mmol), 1,8-diaminooctane (120 mg, 0.80 mmol), BOP (840 mg, 1.9 mmol) and HOBt (260 mg, 1.9 mmol) were dissolved in DMF (15 ml) containing Et$_3$N (0.54 ml, 3.8 mmol). The reaction mixture was stirred for 18 hr at room temperature.

After removal of the solvent, the residue was extracted with AcOEt, which was washed with 10% citric acid, 5% $Na_2CO_3$ and water, dried over $Na_2SO_4$ and concentrated. Petroleum ether was added to the residue to give crystals, which were collected by filtration and recystallized from AcOEt, yield 310 mg (53%), mp 142–144° C., $Rf^1$ 0.56.

Anal. Calcd for $C_{40}H_{62}N_4O_8 \cdot 0.5H_2O$: C, 65.3; 8.62; N, 7.61. Found: C, 65.2; H, 8.40; N, 7.68.

2) 1,8-Bis(Dmt-amino)octane.2TFA

A solution of 1,8-bis($N^\alpha$-Boc-Dmt-amino)octane (260 mg, 1.6 mmol) and anisole (0.1 ml, 0.90 mmol) in TFA (1.0 ml, 13 mmol) was stirred for 1 hr at room temperature. Ether was added to the solution to form a precipitate, which was collected by filtration, dried in vacuo and lyophilized from water, yield 120 mg (60%), $Rf^4$ 0.56, $Rf^5$ 0.68, tR (C) 20.7 min. TOF-MS m/z: 527.7 $(M+1)^+$ (Calcd for $C_{24}H_{34}N_4O_4$: 526.7).

Reference Example 1

1) 1,4-Bis($N^\alpha$-Boc-Phe-amino)butane $N^\alpha$-Boc-Phe-OH (1.1 g, 4.0 mmol), 1,4-diaminobutane (180 mg, 2.0 mmol) and PyBOP (2.5 g, 4.8 mmol) were dissolved in DMF (25 ml) containing $Et_3N$ (0.67 ml, 4.8 mmol). The reaction mixture was stirred for 15 hr at room temperature. After removal of the solvent, AcOEt and water were added to the residue to obtain crystals, which were collected by filtration and recrystallized from EtOH, yield 0.75 g (32%), mp 186–189° C., $Rf^1$ 0.65, $Rf^2$ 0.45.

Anal. Calcd for $C_{32}H_{46}N_4O_6$: C, 66.0; H, 7.96; N, 9.62. Found: C, 65.9; H, 7.75; N, 9.61.

2) 1,4-Bis(Phe-amino)butane.2HCl

A solution of 1,4-bis($N^\alpha$-Boc-Phe-amino)butane (580 mg, 1.0 mmol) and anisole (0.15 ml, 1.4 mmol) in TFA (1.5 ml, 20 mmol) was stirred for 1 hr at room temperature. Ether was added to the solution to form a precipitate, which was collected by filtration. The crude product in 3% AcOH (3 ml) was applied to a Sephadex G-15 column (2.5×43 cm), equilibrated and eluted with 3% AcOH. Fractions (8 g each) were collected and the solvent of the effluent (Nos. 8–11) was removed. The residue was lyophilized from 1 mol/l HCl to yield an amorphous powder, yield 340 mg (75%), $Rf^4$ 0.27, $Rf^5$ 0.47, tR (C) 21.04 min. TOF-MS m/z: 383.3 $(M+1)^+$ (Calcd for $C_{22}H_{30}N_4O_2$: 382.4).

Reference Example 2

1) 1,4-Bis($N^\alpha$-Boc-Tyr-amino)butane $N^\alpha$-Boc-Tyr-OH (5.6 g, 20 mmol), 1,4-diaminobutane (880 mg, 10 mmol), BOP (10.6 g, 24 mmol) and HOBt (3.0 g, 20 mmol) were dissolved in DMF (50 ml) containing $Et_3N$ (5.6 ml. 40 mmol). The reaction mixture was stirred for 15 hr at room temperature. After removal of the solvent, the residue was extracted with AcOEt, which was washed with 5% $Na_2CO_3$ and water, dried over $Na_2SC_4$ and evaporated down. Ether was added to the residue to form a precipitate, which was collected by filtration, yield 4.2 g (68%), mp 123–126° C., $Rf^1$ 0.40.

Anal. Calcd for $C_{32}H_{46}N_4O_8 \cdot 0.7H_2O$: C, 61.3; H, 7.56; N, 8.93. Found: C, 61.4. H, 7.81; N, 8.78.

2) 1,4-Bis(Tyr-amino)butane.2HCl

A solution of 1,4-bis($N^\alpha$-Boc-Tyr-amino)butane (550 mg, 0.90 mmol) and anisole (0.28 ml, 2.6 mmol) in TFA (2.75 ml, 36 mmol) was stirred for 1 hr at room temperature. Ether was added to the solution to form a precipitate, which was collected by filtration and lyophilized from 1 mol/l HCl yield 340 mg (70%), $Rf^4$ 0.27, tR (C) 7.1 min. TOF-MS m/z: 414.1 $M^+$ (Calcd for $C_{22}H_{30}N_4O_4$: 414.4).

Reference Example 3

1) 1,6-Bis($N^\alpha$-Boc-Tyr-amino)hexane $N^\alpha$-Boc-Tyr-OH (5.6 g, 20 mmol), 1,6-diaminohexane (1.9 g, 10 mmol), BOP (11 g, 24 mmol), and HOBt (3.0 g, 20 mmol) were dissolved in DMF (50 ml) containing $Et_3N$ (5.6 ml, 40 mmol). The reaction mixture was stirred for 15 hr at room temperature. After removal of the solvent, the residue was extracted with AcOEt, which was washed with 5% $Na_2CO_3$ and water, dried over $Na_2SO_4$ and evaporated down. Ether was added to the residue to form a precipitate, which was collected by filtration, yield 5.0 g (79%), mp 146–151° C., $Rf^1$ 0.56.

Anal. Calcd for $C_{34}H_{50}N_4O_8 \cdot 2.5H_2O$: C, 59.4; H, 8.06; N, 8.15. Found: C, 59.2; H, 7.84; N, 8.11.

2) 1,6-Bis(Tyr-amino)hexane.2TFA

A solution of 1,6-bis($N^\alpha$-Boc-Tyr-amino)hexane (500 mg, 1.6 mmol) and anisole (0.12 ml, 1.1 mmol) in TFA (1.2 ml, 16 mmol) was stirred for 1 hr at room temperature. Ether was added to the solution to form a precipitate, which was collected by filtration, dried in vacuo and lyophilized from water, yield 250 mg (48%), $Rf^4$ 0.31, tR (Y) 20.1 min TOF-MS m/z: 443.1 $M^+$ (Calcd for $C_{22}H_{30}N_4O_4$:442.5).

Reference Example 4

1) 1,2-Bis($N^\alpha$-Boc-Tyr-amino)ethane $N^\alpha$-Boc-Tyr-OH (4.1 g, 15 mmol), 1,2-diaminoethane (0.36 g, 6.0 mmol) and BOP (7.6 g, 17 mmol) were dissolved in DMF (40 ml) containing $Et_3N$ (2.4 ml, 17 mmol). The reaction mixture was stirred for 15 hr at room temperature. After removal of the solvent, the residue was extracted with AcOEt, which was washed with 5% $Na_2CO_3$ and water, dried over $Na_2SO_4$ and concentrated. Petroleum ether was added to the residue to form a precipitate. The crude product in $CHCl_3$ (5 ml) was applied to a silica gel column (BW-127ZH, 3×34 cm), equilibrated and eluted with $CHCl_3$. After removal of the solvent of the effluent (300–2, 300 ml), petroleum ether was added to the residue to obtain a precipitate, yield 1.0 g (30%), mp 203–206° C., $Rf^1$ 0.49.

Anal. Calcd for $C_{30}H_{42}N_4O_8 \cdot 0.7H_2O$: C, 60.1; H, 7.29; N, 9.34. Found: C, 60.2; H, 6.96; N, 9.03.

2) 1,2-Bis(Tyr-amino)ethane.2TFA

A solution of 1,2-bis($N^\alpha$-Boc-Tyr-amino)ethane (500 mg, 0.90 mmol) and anisole (0.14 ml, 1.3 mmol) in TFA (1.4 ml, 18 mmol) was stirred for 1 hr at room temperature. Ether was added to the solution to form a precipitate. The precipitate was purified with HPLC and lyophilized from water, yield 350 mg (63%), $Rf^4$ 0.30, tR (C) 5.5 min. TOF-MS m/z: 387.0 $(M+H)^+$ (Calcd for $C_{20}H_{26}N_4O_4$: 386.4).

Reference Example 5

1) 1,8-Bis($N^\alpha$-Boc-Tyr-amino)octane $N^\alpha$-Boc-Tyr-OH (5.6 g, 20 mmol), 1,8-diaminooctane (1.4 g, 10 mmol) and BOP (11 g, 24 mmol) were dissolved in DMF (50 ml) containing $Et_3N$ (3.4 ml, 24 mmol). The reaction mixture was stirred for 15 hr at room temperature. After removal of the solvent, the residue was extracted with AcOEt, which was washed with 5% $Na_2CO_3$ and water, dried over $Na_2SO_4$ and concentrated. Petroleum ether was added to the residue to form a precipitate, which was collected by filtration, yield 6.1 g (91%), mp 159–160° C., $Rf^4$ 0.60.

Anal. Calcd for $C_{36}H_{54}N_4O_8 \cdot 0.5H_2O$: C, 63.6; H, 8.09; N, 8.23. Found: C, 63.9; H, 8.23; N, 7.97.

2) 1,8-Bis(Tyr-amino)octane.2TFA

A solution of 1,8-bis($N^\alpha$-Boc-Tyr-amino)octane (1.0 g, 1.5 mmol) and anisole (0.45 ml, 4.2 mmol) in TFA 4.5 ml, 60 mmol) was stirred for 1 hr at room temperature. Ether was added to the solution to form a precipitate, which was purified with HPLC and lyophilized from water, yield 320 mg (30%), Rf⁴ 0.30, tR (C) 18.3 min. TOF-MS m/z: 471.2 (M+1)⁺ (Calcd for $C_{26}H_{38}N_4O_4$: 470.4).

Reference Example 6
Boc-Dmt-OH 2,6-Dimethyl-L-tyrosine mono hydrochloride (4.7 g, 0.018 mol) was dissolved in water and thereto was added triethylamine (4.9 ml, 0.036 mol). Di-t-butyldicarbonate (3.9 g, 0.020 mol) in dioxane (20 ml) was added to the above solution. The solution was stirred overnight at room temperature. After the reaction, the solvent was removed and the residual oil was suspended in citric acid solution. The suspension was extracted with AcOEt. The organic layer was washed with saturated brine and water and then dried over sodium sulfate. The solvent was removed and to the residue was added hexane to form a precipitate. The precipitate was collected by suction to give Boc-Dmt-OH (yield 5.5 g). mp 174–177° C., Rf⁴ 0.80, $[\alpha]_D^{25}$=−11.0(C=1, MeOH)

Anal. Calcd for $C_{16}H_{23}NO_5 \cdot 0.1H_2O$: C, 61.8; H, 7.51; N, 4.50. Found: C, 61.8; H, 7.54; N, 4.45.

Regarding the opioid peptide derivatives of the present invention, as shown in the following Experimental Examples, the opioid receptor affinity was measured by performing a receptor competitive assay using mouse brain-derived opioid receptors, whether the derivative is an agonist or an antagonist was tested by a guinea pig ileum (GPI) method and a mouse seminiferous tract (MVD) method, and finally the analgesic effect was measured by a Tail Pressure method and, whereby, the pharmacological effects of the present opioid peptide derivatives were confirmed.

Experimental Example 1
Measurement of the Opioid Receptor Affinity:

Regarding the opioid peptide derivatives synthesized in Examples and Reference Examples, the μ- and δ-opioid receptor affinities were obtained by a competitive receptor assay using the synaptic membrane fraction obtained from the rat brain tissue according to the known methods. That is, Sprague-Dawley rats having an average weight of 150–180 g were killed by decapitation, the brain tissue from which cerebellum had been removed was homogenized in 0.32M sucrose and 1 mM HEPES (pH 7.5) containing 50 μg/ml soybean trypsin inhibitor, fractionated and centrifuged to obtain the synaptic membrane fraction (P2 fraction), which was pre-incubated in 50 mM HEPES (pH 7.5) containing 100 mM NaCl, 0.1 mM GDP and soybean trypsin inhibitor to remove endogenous ligands from the P2 fraction.

A competitive receptor binding assay (Radiolabeled receptor assay: RRA) based on an exchange reaction between a radioactive ligand for the synaptic membrane fraction and a peptide derivative to be tested was performed by using tritium-labeled [³H]DAGO which is a μ-opioid receptor agonist and tritium-labeled [³H]DPDPE which has the high δ-opioid receptor selectivity, and incubating an aliquot of the synaptic membrane with the peptide derivative to be tested for a period of time. Upon this, an exchange reaction between a ligand was performed under constant conditions, the radiation remaining in the synaptic membrane fraction was measured, and an amount of the ligand adsorbed onto the synaptic membrane fraction is calculated. By assuming that binding with a receptor occurs in competition between a radioactive ligand and an end ligand, the concentration ($IC_{50}$) at which the maximum specific binding of the radioactive ligand is 50% inhibited was obtained, from which the affinity constant (Ki) was calculated by a method of Cheng et al. (Biochem. Pharmcol., 22, 3099 (1973)).

The results are shown in the following Table.

TABLE 1

Affinity and selectivity of compounds on μ- and δ- receptors

| Compound | Affinity and selectivity of receptor (Ki, nM) | | |
|---|---|---|---|
| | δ | μ | δ/μ |
| Ref.ex.2: TyrN H—(CH₂)₄—NHTyr | 6,500 ± 278 | 309 ± 104 | 21 |
| Ref.ex.1: PheN H—(CH₂)₄—NHPhe | 46,200 ± 458 | 1,530 ± 122 | 30 |
| Ex.2: DmtNH—(CH₂)₄—NHPhe | 61.0 ± 5.7 | 0.52 ± 0.089 | 117 |
| Ex.3: DmtNH—(CH₂)₄—NHTyr | 133 ± 18 | 0.38 ± 0.02 | 349 |
| Ex.1: DmtNH—(CH₂)₄—NHDmt | 53.4 ± 14.8 | 0.041 ± 0.003 | 1300 |
| Ref.ex.4: TyrN H—(CH₂)₂—NHTyr | 8,290 ± 43.3 | 648 ± 95 | 13 |
| Ex.5: DmtNH—(CH₂)₂—NHDmt | 116 ± 10.6 | 1.43 ± 0.01 | 81 |
| Ref.ex.3: TyrN H—(CH₂)₆—NHTyr | 21,900 ± 4,020 | 410 ± 85 | 53 |
| Ex.4: DmtNH—(CH₂)₆—NHDmt | 46.1 ± 8.8 | 0.053 ± 0.01 | 870 |
| Ref.ex.5: TyrN H—(CH₂)₈—NHTyr | 6,150 ± 525 | 399 ± 40.5 | 34 |
| Ex.6: DmtNH—(CH₂)₈—NHDmt | 14.8 ± 3.0 | 0.19 ± 0.024 | 78 |

It was confirmed that compounds of the present invention have the affinity for a μ-receptor at the very low concentration.

Experimental Example 2

Measurement of the agonist and antagonist activities on various opioid receptors:

An assay test for agonist and antagonist activities of opioid compounds was performed using guinea pig ileum (GPI) and mouse seminiferous tract (MVD). That is, male guinea pigs having the weight of around 300 g were killed by exsanguination, an ileum section having a length of around 10 cm was isolated from an ileum close to an ileum-caecum region was held at 36° C. The ileum section was placed in a Magnus tube treated with an oxygen mixture (95% O₂/5% CO₂) and filled with Krebs solution in the state where the rest tension of 1 g was applied with an isotonic transducer and, then, was performed. Then, the electrical stimulation was applied at 30V for 0.5 ms. via electrode previously installed in the Magnus tube to constrict guinea pig ileum longitudinal muscle and, after constriction was stabilized, a peptidase inhibitor was added. Then, the present peptide derivative to be tested was added, the constriction of guinea pig ileum longitudinal muscle was taken by Grass-FTO 0.3 transducer and monitored by an amplifier and a recorder connected to the transducer. The opioid activity was determined by constriction inhibition after addition of the peptide derivative to be tested and constriction inhibition cancellation by addition of naloxone, a selective opioid antagonist. The concentration at which the constriction by electrical stimulation of guinea pig ileum longitudinal muscle is 50% inhibited was measured, which was used as $IC_{50}$.

In addition, in a mouse MVD assay, the similar procedures were carried out using mouse seminiferous tract in place of guinea pig ileum, and the concentration $IC_{50}$ at which the constriction by electrical stimulation of mouse seminiferous tract is 50% inhibited was determined.

Since it was made clear that the opioid activity is mediated mainly by μ-opioid receptor in a GPI assay, whereas inhibition of the electrical constriction is by the interaction with δ-opioid receptor, the concentration at which each constriction by electrical stimulation was 50% inhibited was regarded as the agonist effect.

The results obtained on the present peptide derivatives are shown in following Table.

TABLE 2

Agonist and antagonist activities of compounds on μ- and δ- receptors

| Compound | Agonist and antagonist activities (nM) | | |
|---|---|---|---|
| | GPI(IC$_{50}$ ± S.E.) | MVD(IC$_{50}$ ± S.E.) | |
| Ex.2: DmtNH—(CH$_2$)$_4$—NHPhe | 181 ± 36 | >10000 | ant. (5.5) |
| Ex.3: DmtNH—(CH$_2$)$_4$—NHTyr | 225 ± 11 | >10000 | ant. (5.3) |
| Ex.1: DmtNH—(CH$_2$)$_4$—NHDmt | 5.33 ± 0.65 | >10000 | ant. (5.8) |
| Ex.5: DmtNH—(CH$_2$)$_2$—NHDmt | 2840 ± 517 | >10000 | ant. (5.5) |
| Ex.4: DmtNH—(CH$_2$)$_6$—NHDmt | 3.08 ± 0.53 | >10000 | ant. (6.1) |
| Ex.6: DmtNH—(CH$_2$)$_8$—NHDmt | 53.7 ± 7 | >10000 | ant. (6.4) |

NT: Not tested

From these results, it can be seen that the present peptide derivatives are μ-receptor agonists.

The analgesic effects of 1,4-bis(2,6-dimethyl-L-tyrosylamino)butane (Ex. 1) and 1,6-bis(2,6-dimethyl-L-tyrosylamino)hexane (Ex. 4):

These compounds are novel compounds synthesized by the present inventors. These compounds have been shown to have the high μ receptor binding properties from a binding experiment to an opioid receptor of a synaptic membrane fraction. In addition, these compounds are recognized to have the agonist activity to guinea ileum in an experiment using a section of guinea pig gut tract. Therefore, it is presumed that these compounds have the analgesic effects. Then, these compounds were administered intracerebroventricularly (i.v.c.), intravenously or subcutaneonsly into a rat, and the analgesic effects were examined.

Method;

SD Male rats, weighing 110 to 130 g, were used. One group consisted of five rats. The analgesic effects were examined by a Randoll-Seritto method. That is, the pressure was applied to a hind limb of a rat using a pressure-stimulated analgesic effect measuring apparatus, and the threshold at which a rat exhibits an escape reaction was measured, which was used as an index for the analgesic effect. The threshold was expressed in mm Hg. During the measurement, the upper limit of the pressure applied to a hind limb was 100 mm Hg in order to avoid damage of the tissues.

1) When performing intracerebroventricular administration (i.c.v.), a rat was fixed to a brain stereotactic fixing apparatus under slight ether anesthesia, the skin at a head was dissected, and an administration cannula was inserted into a place at a transverse of 1.5 to 2.0 nm from a bregma position and a depth of 3.5 to 4.0 mm. The administration volume was 10 μl/animal. Observation of the analgesic action was performed before administration, and at 30 minutes, and 1, 2, 3, 4 and 5 hours after administration. Doses of both compounds were 0.1, 1 and 10 μg/animal. Separately, a group to which 5 mg/kg of naltrexone hydrochloride was administered subcutaneously immediately after compound of Ex.1 10 μg/animal i.c.v and a group to which 5 mg/kg of naltrexone hydrochloride was administered subcutaneously immediately after compound of Ex.4 10 μg/animal i.c.v. was made. In addition, as morphine hydrochloride at a dose of 3 μg/animal i.c.v. group was used as a positive control group and a physiological saline 10 μl/animal i.c.v. group as a control group was made, respectively.

2) When administered intravenously (i.v.), a volume of 2 ml/kg weight was administered to a tail vein and, when administered subcutaneously (s.c.), a volume of 2 ml/kg weight was subcutaneously administered to the back. In the case of intravenous administration, a 1 mg/kg, 3 mg/kg or 10 mg/kg compound of Ex.1 administration group, a 1 mg/kg, 3 mg/kg or 10 mg/kg compound of Ex.4 administration group, a 2 ml/kg physiological saline administration group and a 5 mg/kg morphine hydrochloride administration group were made, respectively. In the case of subcutaneous administration, a 10 mg/kg, 30 mg/kg or 100 mg/kg compound of Ex.1 administration group, a 10 mg/kg, 30 mg/kg or 100 mg/kg compound of Ex.4 administration group, a 2 ml/kg physiological saline administration group and a 5 mg/kg morphine hydrochloride administration group were made, respectively. Observation of the analgesic action was performed 15 minutes, 30 minutes, 1 hour and 2 hours after administration in the case of intravenous administration, 30 minutes, 1 hour, 2 hours and 3 hours after administration in the case of subcutaneous administration, respectively.

In order to perform a significant difference test between respective administration groups and control groups, and between values at respective times before administration and after administration, a Dunnet multiple comparative test method was used. In the statistical processing for performing a significant difference test between morphine hydrochloride administration groups and control groups, Student t-test was used. For performing a significant difference test between values at respective times before administration and after administration in morphine hydrochloride administration groups, a Dunnet multiple comparative test method was used. A significant level was at 5 or lower % risk rate (two-tailed test).

Results by intracerebroventricular administration are shown in following Table 3.

TABLE 3

Effects in rats (intracerebroventricularly)

| | | Threshold (mmHg) | | | | | | |
|---|---|---|---|---|---|---|---|---|
| | Dose | | Time After administration (hr) | | | | | |
| Drugs | (μg/animal, i.c.v.) | Before | 0.5 | 1 | 2 | 3 | 4 | 5 |
| Control[a] | — | 47 ± 1 | 46 ± 1 | 46 ± 1 | 48 ± 1 | 45 ± 1 | 46 ± 1 | 46 ± 2 |
| Ex. 1 | 0.1 | 47 ± 1 | 47 ± 1 | 50 ± 2 | 50 ± 1 | 48 ± 2 | 48 ± 1 | 49 ± 1 |

TABLE 3-continued

Effects in rats (intracerebroventricularly)

| | | | Threshold (mmHg) | | | | | |
|---|---|---|---|---|---|---|---|---|
| | Dose | | Time After administration (hr) | | | | | |
| Drugs | (μg/animal, i.c.v.) | Before | 0.5 | 1 | 2 | 3 | 4 | 5 |
| Ex. 1 | 1 | 47 ± 2 | 51 ± 3 | 54 ± 3 | 49 ± 1 | 49 ± 2 | 48 ± 2 | 47 ± 1 |
| Ex. 1 | 10 | 48 ± 2 | 61 ± 8*,$ | 61 ± 5**,$ | 54 ± 4 | 51 ± 3 | 52 ± 2 | 52 ± 1* |
| Ex. 1 + Naltrexon | 10 + 5 mg/kg, s.c. | 47 ± 2 | 49 ± 1 | 53 ± 3 | 54 ± 2 | 52 ± 2 | 49 ± 1 | 50 ± 1 |
| Ex. 4 | 0.1 | 45 ± 2 | 47 ± 2 | 47 ± 1 | 50 ± 2 | 49 ± 2 | 49 ± 2 | 47 ± 1 |
| Ex. 4 | 1 | 46 ± 1 | 51 ± 2 | 51 ± 2 | 51 ± 3 | 50 ± 2 | 53 ± 2*,$ | 52 ± 1*,$ |
| Ex. 4 | 10 | 46 ± 1 | 50 ± 2 | 47 ± 0 | 49 ± 2 | 48 ± 2 | 48 ± 2 | 49 ± 1 |
| Ex. 4 + Naltrexon | 10 + 5 mg/kg, s.c. | 46 ± 1 | 55 ± 2*,$ | 52 ± 2*,$ | 51 ± 2 | 51 ± 1 | 52 ± 1*,$ | 50 ± 1 |
| Morphine | 3 | 46 ± 1 | 59 ± 4# | 59 ± 3## | 52 ± 3 | 52 ± 3# | 49 ± 2 | 51 ± 2 | i.c.v: intracerebroventricularly Each value represents the mean ± S.E. (n = 5).
a)distilled water (10 μL/ animal, i.c.v.).
* and **significant difference from control group at P < 0.05 and P < 0.01, respectively (Dunnett's test).
# and ##significant difference from control group at P < 0.05 and P < 0.01, respectively (Student's t-test).
$significant difference from before group at p < 0.05 (Dunnett's test).

In the physiological saline administration group, a significant change was not seen in the escape reaction threshold at any time after administration. In the case where morphine hydrochloride 3 μg/animal was administered, a significant increase in the threshold was recognized 30 minutes, 1 hour and 3 hours after administration as compared with before administration.

any time after administration. In the group where 5 mg/kg of naltrexone was administered subcutaneouly immediately after administration of 10 μg of compound of Ex.4, a significant increase in the threshold was seen 30 minutes, 1 hour and 4 hours after administration.

Results by intravenous administration are shown in

TABLE 4

Effects in rats (intraveneous).

| | | | Threshold (mmHg) | | | |
|---|---|---|---|---|---|---|
| | Dose | | Time after administration (hr) | | | |
| Drugs | (mg/kg, i.v.) | Before | 0.25 | 0.5 | 1 | 2 |
| Control a) | — | 48 ± 2 | 48 ± 2 | 50 ± 2 | 51 ± 2 | 49 ± 2 |
| Ex. 1 | 1 | 48 ± 2 | 50 ± 2 | 54 ± 2 | 53 ± 3 | 56 ± 2$ |
| Ex. 1 | 3 | 48 ± 2 | 55 ± 2 | 56 ± 3 | 52 ± 4 | 49 ± 2 |
| Ex. 1 | 10 | 48 ± 2 | 60 ± 2**,$$ | 56 ± 3 | 54 ± 2 | 53 ± 2 |
| Ex. 1 | 1 | 48 ± 2 | 47 ± 2 | 51 ± 3 | 51 ± 3 | 51 ± 3 |
| Ex. 4 | 3 | 48 ± 2 | 57 ± 4 | 54 ± 3 | 54 ± 5 | 53 ± 3 |
| Ex. 4 | 10 | 49 ± 2 | 54 ± 3 | 53 ± 3 | 57 ± 2 | 52 ± 2 |
| Morphine | 5 | 49 ± 2 | 83 ± 6##,$$ | 79 ± 7##,$$ | 78 ± 6##,$$ | 65 ± 7 |

Each value represents the mean ± S.E. (n = 5).
a)saline (2 mL/kg, i.v.).
* and **significant difference from control group at P < 0.05 and P < 0.01, respectively (Dunnett's test).
# and ##significant difference from control group at P < 0.05 and P < 0.01, respectively (Student's t-test).
$ and $$significant difference from each before group at P < 0.05 and P < 0.01, respectively (Dunnett's test).

In compound of Ex.1 administration group, a significant increase in the threshold was seen in the 10 μg/administration group 30 minutes and 1 hour after administration as compared with before administration. Increase in the threshold seen in compound of Ex.1 10 μg administration group was dissipated by naltrexone 5 mg/kg subcutaneous administration. On the other hand, regarding compound of Ex.4, a significant increase in the threshold was seen 4 hours and 5 hours after administration in the 1 μg/animal administration group. However, in the 10 μg/animal administration group, a significant change in the threshold was not seen at In the physiological saline administration group, a significant change in the escape reaction threshold was not seen at any time after administration. In morphine hydrochloride 5 mg/kg administration group, a significant increase in the escape reaction threshold was recognized 15 minutes, 30 minutes and 1 hour after administration as compared with before administration.

In compound of Ex.1 administration group, a significant increase in the threshold was seen 15 minutes after administration in the 10 mg/kg administration group. In compound of Ex.4 administration group, a significant change in the threshold was not seen at any measuring time at any dose.

Results by subcutaneous administration are shown in following Table 5.

TABLE 5

Effects in rats (subcutaneous).

| Drugs | Dose (mg/kg, s.c.) | Threshold (mmHg) | | | | |
|---|---|---|---|---|---|---|
| | | Before | Time after administration (hr) | | | |
| | | | 0.5 | 1 | 2 | 3 |
| Control[a] | — | 47 ± 2 | 49 ± 3 | 52 ± 2 | 48 ± 2 | 50 ± 3 |
| Ex. 1 | 10 | 47 ± 2 | 55 ± 5 | 62 ± 6 | 58 ± 3* | 57 ± 2 |
| Ex. 1 | 30 | 47 ± 2 | 52 ± 4 | 65 ± 5$$ | 68 ± 3**,$$ | 59 ± 4 |
| Ex. 1 | 100 | 47 ± 2 | 86 ± 2**,$$ | 77 ± 2**,$$ | 77 ± 2**,$$ | 70 ± 3**,$$ |
| Ex. 4 | 10 | 47 ± 2 | 58 ± 3 | 58 ± 5 | 55 ± 5 | 53 ± 1 |
| Ex. 4 | 30 | 47 ± 2 | 59 ± 3 | 56 ± 3 | 65 ± 5$$ | 59 ± 4 |
| Ex. 4 | 100 | 48 ± 2 | 69 ± 6**,$$ | 68 ± 3*,$ | 75 ± 8**,$$ | 58 ± 2 |
| Morphine | 5 | 48 ± 2 | 87 ± 2##,$$ | 85 ± 6##,$$ | 71 ± 7#,$ | 61 ± 7 |

Each value represents the mean ± S.E. (n = 5).
[a] saline (2 mL/kg, s.c.).
* and **significant difference from control group at $P < 0.05$ and $P < 0.01$, respectively (Dunnett's test).
# and ##significant difference from control group at $P < 0.05$ and $P < 0.01$, respectively (Student's t-test).
$ and $$significant difference from each before group at $P < 0.05$ and $P < 0.01$, respectively (Dunnett's test).

In the physiological saline administration group, a significant change in the escape reaction threshold was not seen at any time after administration. In morphine hydrochloride 5 mg/kg administration group, a rapid increase in the threshold was seen and a significant increase was recognized 30 minutes, 1 hour and 2 hours after administration as compared with before administration. However, 3 hours after administration, a significant increase in the threshold was not seen.

In compound of Ex.1 10 mg/kg administration group, a tendency of an increase in the threshold was seen. However, 2 hours after administration, only a significant difference between control groups was seen 2 hours after administration. In the 30 mg/kg administration group, a significant increase in the threshold was seen 1 hour and 2 hours after administration as compared with before administration. In the 100 mg/kg administration group, the similar increase in the threshold to that in the case of morphine 5 mg/kg administration was seen, and a significant increase was seen at any measuring time after administration as compared with before administration.

In compound of Ex.4 10 mg/kg administration group, although a tendency of a slight increase in the threshold was seen, a significant difference was not seen before administration and between control groups. In the 30 mg/kg administration group, the threshold was gradually increased, and a significant increase was seen 2 hours after administration as compared with the values before administration. In the 100 mg/kg administration group, the threshold was increased rapidly, and a significant difference was seen in the measured values 30 minutes, 1 hour and 2 hours after administration as compared with the values before administration. However, 3 hours after administration, a significant increase was not seen.

Also in the case of intravenous administration, compound of Ex.1 10 mg/kg exhibited an analgesic effect but is weaker as compared with the case of morphine 10 mg/kg administration and its duration time was shorter. On the other hand, no analgesic effect was seen in compound of Ex.4 at all doses used in the experiment.

When subcutaneously administered, both compound of Ex.1 and compound of Ex.4 exhibited the analgesic effect. 10 mg/kg of compound of Ex.1 is weaker 2 hours after administration but exhibited the significant analgesic effect as compared with control groups. This analgesic effect was exhibited earlier, became stronger and has a longer duration time by increasing the dose. The analgesic effect by compound of Ex.1 100 mg/kg subcutaneous administration is approximately comparative to the effect by morphine 5 mg/kg subcutaneous administration, and an effect duration time was longer than in morphine. Compound of Ex.4 30 mg/kg subcutaneous administration exhibited the significant analgesic effect 2 hours after administration. At the 100 mg/kg administration, the significant analgesic effect was exhibited from 30 minutes after administration. The analgesic effect of compound of Ex.4 was weaker and has a shorter duration time than in compound of Ex.1. That it took a time before manifestation of the action and a duration time of the effect was prolonged with increasing doses shows a possibility that these compounds are absorbed comparatively slowly from a subcutaneous administration site or metabolites of these compound have the analgesic action.

From the above experimental results, it was made clear that compound of Ex.1 and compound of Ex.4 have the analgesic effect via the $\mu$-opioid receptor.

The peptide derivatives represented by the formula (1) and salts thereof in accordance with the present invention are novel compounds not described in the prior art, have the specific affinity for the opioid receptor, and manifest a variety of morphine-like physiological activities such as the analgesic effect.

Accordingly, the peptide derivatives (1) of the present invention and salts thereof can be used as an analgesic drug or drugs for treating or preventing nervous diseases associated with other opioid receptor activities.

What is claimed is:

1. A peptide derivative represented by the following formula (1) or a salt thereof:

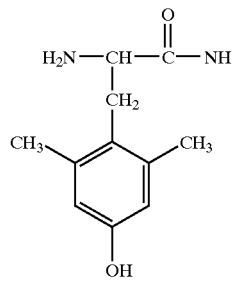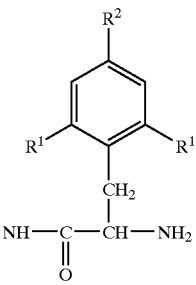

(1)

wherein $R^1$ is hydrogen atom or methyl group, $R^2$ is hydroxy group and n is an integer of 1 to 8.

2. The peptide derivative represented by the formula (1) or a salt thereof claimed in claim 1, wherein $R^1$ is methyl group.

3. The peptide derivative represented by the formula (1) or a salt thereof claimed in claim 1 or 2, wherein n is an integer of 4 to 6.

4. A pharmaceutical composition containing a peptide derivative represented by the formula (1) or a salt thereof claimed in claim 1 or 2 as an active ingredient.

5. A method for inhibiting or moderating pain comprising administering a peptide derivative represented by the formula (1) or a salt thereof claimed in claim 1 or 2 in an effective dosage to a patient having pain.

6. A method for inhibiting or moderating the pain comprising administering a peptide derivative represented by the formula (1) or one salt thereof claimed in claim 1 or 2 in an effective dosage to a patient having pain or suffering from nervous defect disease related to $\mu$-opioid receptor activation.

* * * * *